US00PP08227P

United States Patent [19]

van der Knapp

[11] Patent Number: Plant 8,227

[45] Date of Patent: May 11, 1993

[54] CHRYSANTHEMUM PLANT — ALHA CULTIVAR

[75] Inventor: Jacques C. M. van der Knapp, De Lier, Netherlands

[73] Assignee: Fides Beheer B.V., De Lier, Netherlands

[21] Appl. No.: 720,725

[22] Filed: Jun. 25, 1991

[51] Int. Cl.[5] ..... A01H 5/00

[52] U.S. Cl. ..... Plt./82.2

[58] Field of Search ..... Plt./74.1, 82.2

[56] References Cited

U.S. PATENT DOCUMENTS

P.P. 6,303 9/1988 van der Knaap ..... Plt. 82.2
P.P. 6,774 5/1989 VandenBerg ..... Plt. 82.2
P.P. 6,879 6/1989 Suepitz ..... Plt. 82.2

OTHER PUBLICATIONS

Sunnyslope Gardens, "Chrysanthemums 1992", p. 3.
Sunnyslope Gardens, "Chrysanthemums 1991", p. 3.
Sunnyslope Gardens, "Chrysanthemums '82", p. 3.

*Primary Examiner*—Howard J. Locker
*Attorney, Agent, or Firm*—Burns, Doane, Swecker & Mathis

[57] ABSTRACT

A new and distinct cultivar of Chrysanthemum plant named ALHA is provided. The new cultivar was the result of a controlled breeding program wherein the Frankfort cultivar (U.S. Plant Pat. No. 6,342) was pollinated by the Penny Lane cultivar (U.S. Plant Pat. No. 6,238). More specifically, the new cultivar forms attractive yellow spider anemone flowers having a small cushion at the center and tubular ray florets which end in a spoon-like configuration (as illustrated). The disc florets when immature are yellow-green and change to yellow when mature. The inflorescence is of the generally flat capitulum form. The response period of the flowers is approximately eight weeks. Resistance to white rust has been exhibited. The new cultivar is particularly suited for use in the production of a cut spider anemone spray under greenhouse conditions.

1 Drawing Sheet

SUMMARY OF THE INVENTION

The present inventiton comprises a new and distinct cultivar of Chrysanthemum, botanically known as *Chrysanthemum morifolium.*, Ramat., and hereinafter is referred to by the cultivar name ALHA.

The new cultivar is the product of a planned breeding program which had as its objective the creation of a new Chrysanthemum cultivar which exhibits attractive yellow spider anemone flowers, a flower response period of approximately eight weeks, white rust resistance, and the ability to produce flowers of commercially acceptable quality throughout the year in a cut mum production program. Such combination of traits is not believed to have been present in the previously available Chrysanthemum cultivars. This objective was satisfactorily fulfilled in the cultivar of the present invention.

The breeding program which resulted in the production of the new cultivar of the present invention was carried out in a controlled environment during 1984 at De Lier, The Netherlands. The female parent (i.e., the seed parent) was the Frankfort cultivar (U.S. Plant Pat. No. 6,342) and the male parent (i.e., the pollen parent) was the Penny Lane cultivar (U.S. Plant Pat. No. 6,238). The parentage of the new cultivar can be summarized as follows:

Frankfort × Penny Lane.

The seeds resulting from the above pollination were sown and plantlets were obtained which were physically and biologically different from each other. Selective study during October, 1985 resulted in the identification of a single parent of the new variety.

It was found that the new cultivar of the present invention:

(a) exhibits attractive yellow spider anemone flowers having a small cushion at the center and tubular ray florets which end in a spoon-like configuration,
(b) bears flowers of a generally flat capitulum form,
(c) exhibits a flower response period of approximately eight weeks,
(d) exhibits resistance to white rust,
(e) forms attractive dark green foliage, and
(f) has the ability to produce flowers of commercially acceptable quality throughout the year in a cut mum production program.

Asexual reproduction of the new cultivar by cuttings initially taken during November, 1985, as performed at De Lier, The Netherlands, in a controlled environment has demonstrated that the characteristics of the new cultivar as herein disclosed are firmly fixed and are retained through successive generations of asexual propagation.

ALHA has not been observed under all possible environmental conditions to date. Accordingly, it is possible that the phenotype may vary somewhat with variations in the environment, such as temperature, light, day length, contact with pesticides and/or subjection to growth retardant treatments.

When the new cultivar of the present invention is compared to the Yellow Frost cultivar (U.S. Plant Pat. No. 4,220), the ALHA cultivar is found to form more vegetative growth (e.g., assumes a height of approximately 100 cm. vs. approximately 88 cm.), exhibits a smaller overall flower diameter (e.g., approximately 60 to 70 mm. vs. approximately 80 mm.), and exhibits shorter ray florets with smaller spoons. The flower type, response time, and foliage of the ALHA cultivar are substantially identical to those of the Yellow Frost cultivar.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at De Lier, The Netherlands.

DETAILED DESCRIPTION

The chart used in the identification of colors described hereafter is The R.H.S. Colour Chart of The Royal Horticultural Society, London, England. The color values were determined at 11:00 a.m. to 12:00 noon under natural daylight conditions at De Lier, The Netherlands, on Mar. 13, 1991. The plants described were grown under standard greenhouse conditions which approximate those commonly utilized for the production of cut mums.

Classification:

*Botanical.*—*Chrysanthemum morifolium* Ramat., cv. ALHA.

*Commercial.*—Cut anemone spray.

Inflorescence

A. Capitulum:

*Form.*—Generally flat capitulum form.

*Type.*—Spider anemone.

*Diameter across face.*—Approximately 60 to 70 mm. on average.

*Diameter of flower center.*—Approximately 25 mm. on average.

B. Corolla of ray and disc florets:

*Color (General tonality from a distance of three meters).*—Yellow.

*Color ray florets.*—(Top surface). — Yellow, Yellow-Orange Group 16B. (Under surface). — Yellow, Yellow-Orange Group 16B.

*Color disc florets.*—Yellow-Green Group 149A when immature, changing to Yellow-Orange Group 15A when mature.

C. Reproductive organs:

*Androecium.*—Present in disc florets.

*Gynoecium.*—Present in disc florets.

Plant

A. General appearance:

*Height.*—Approximately 100 cm. on average.

B. Foliage:

*Color (upper surface).*—Yellow-Green Group 147A.

*Color (under surface).*—Yellow-Green Group 147B.

I claim:

1. A new and distinct cultivar of Chrysanthemum plant named ALHA, substantially as herein shown and described, which:

(a) exhibits attractive yellow spider anemone flowers having a small cushion at the center and tubular ray florets which end in a spoon-like configuration, (b) bears flowers of a generally flat capitulum form, (c) exhibits a flower response period of approximately eight weeks, (d) exhibits tolerance to white rust, (e) forms attractive dark green foliage, and (f) has the ability to produce flowers of commercially acceptable quality throughout the year in a cut mum production program.

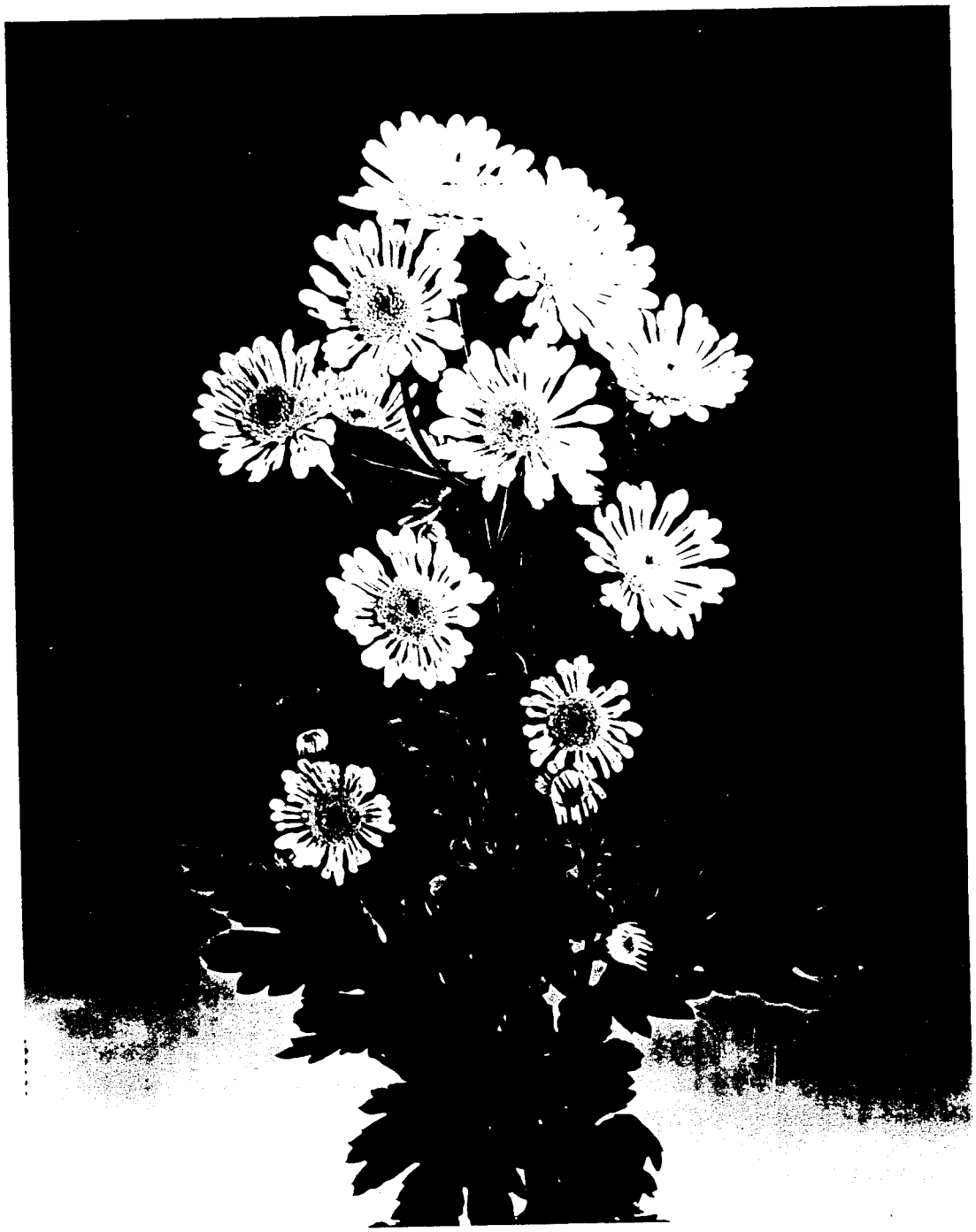

* * * * *